United States Patent [19]

Herczog et al.

[11] 4,248,231

[45] Feb. 3, 1981

[54] SURGICAL CUTTING INSTRUMENT

[75] Inventors: Andrew Herczog, Hammondsport; James A. Murphy, Painted Post, both of N.Y.

[73] Assignee: Corning Glass Works, Corning, N.Y.

[21] Appl. No.: 961,189

[22] Filed: Nov. 16, 1978

[51] Int. Cl.³ .............................................. A61B 17/39
[52] U.S. Cl. ............................ 128/303.14; 128/303.17
[58] Field of Search ............ 128/303.1, 303.13, 303.14, 128/303.17, 303.18, 783, 784, 799, 800, 804

[56] References Cited

U.S. PATENT DOCUMENTS

| Re. 29,088 | 12/1976 | Shaw | 128/303.17 |
|---|---|---|---|
| 3,970,088 | 7/1976 | Morrison | 128/303.14 |
| 3,987,795 | 10/1976 | Morrison | 128/303.14 |
| 4,033,351 | 7/1977 | Hetzel | 128/303.14 |
| 4,043,342 | 8/1977 | Morrison, Jr. | 128/303.14 |
| 4,161,950 | 7/1979 | Doss et al. | 128/303.14 |

FOREIGN PATENT DOCUMENTS

| 2303515 | 10/1976 | France | 128/303.1 |
|---|---|---|---|
| 2303517 | 10/1976 | France | 128/303.1 |

*Primary Examiner*—Lee S. Cohen
*Attorney, Agent, or Firm*—John P. DeLuca; Burton R. Turner

[57] ABSTRACT

The present invention provides a surgical cutting instrument having a blade portion and cutting edge therefor with electric input elements located near the cutting edge for cutting the tissue and cauterizing the surfaces of the incision, thereby allowing surgery to be more rapidly performed. This is accomplished in accordance with the illustrated embodiments of this invention by providing electrodes of opposed polarity, applied to the blade, near the cutting edge. With an electrical potential applied, no current will flow between the electrodes and no heat is produced unless the electrode gap is bridged by a conducting medium such as a high conductivity physiological liquid from the incision. Heat is then generated by electric discharge below an arcing threshold in all areas where the blade is in contact with moist tissue. No electric discharge or heat occurs elsewhere. Moreover, if movement of the blade is halted, heat generation will automatically diminish as the cut tissue becomes dry as a result of cauterization.

6 Claims, 5 Drawing Figures

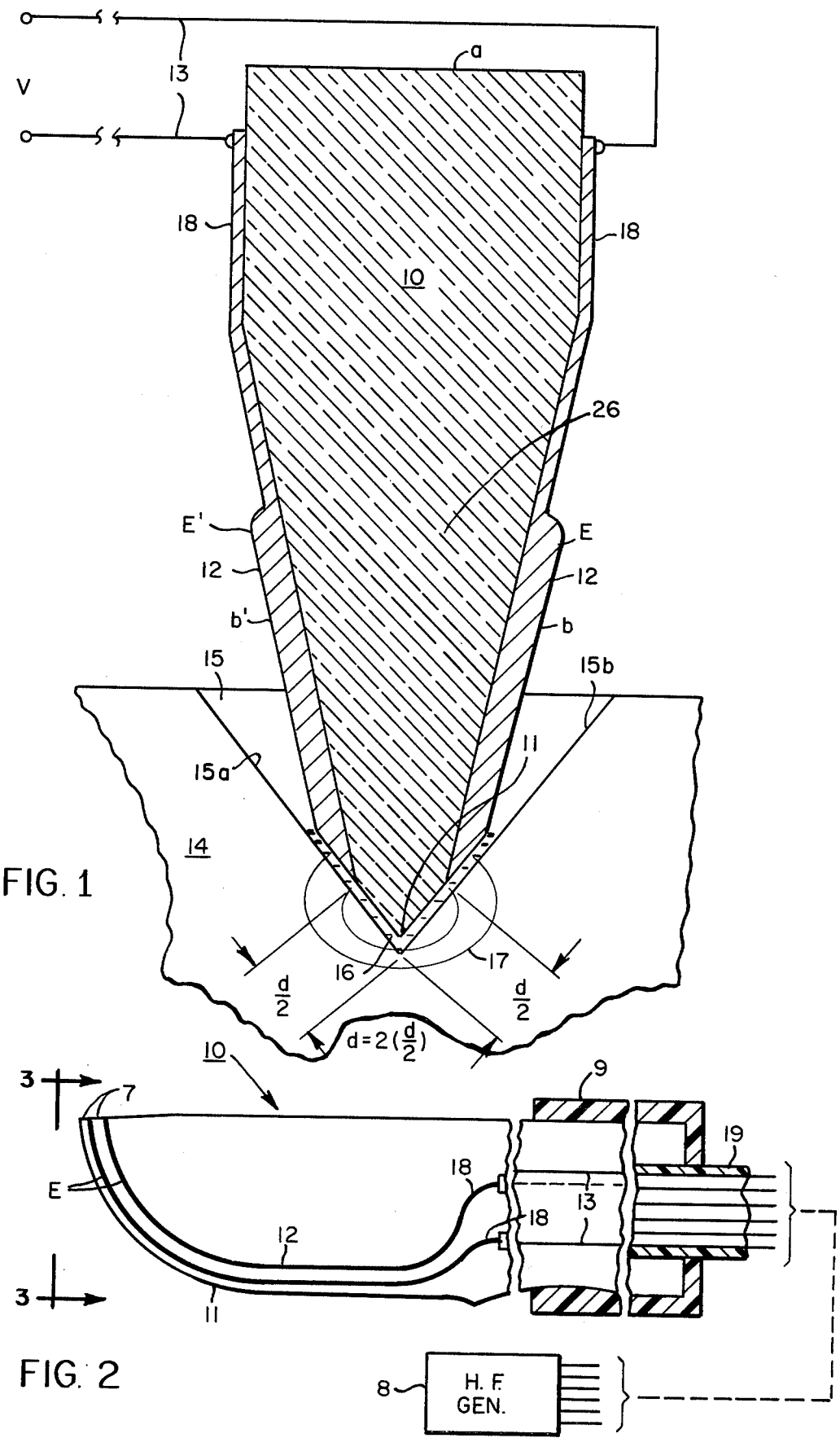

SURGICAL CUTTING INSTRUMENT

BACKGROUND OF THE INVENTION

During application of a surgical knife or scalpel bleeding can be reduced by cauterizing the cut tissue through heat. According to the prior art, this can be obtained, for example, by applying resistance elements near the cutting edge of the scalpel which is electrically heated to provide a temperature of 200°–500° C. in contact with the tissue. In doing so, however, parts of the blade not in contact with tissue may become grossly overheated, presenting a hazard to both patient and surgeon. Several methods have been recommended to overcome this problem. Generally, all have disadvantages. For example, segmented heating elements require individual temperature-power control systems; heating elements with a large negative temperature coefficient of resistance (TCR) require a very high voltage drive; and, high frequency electric discharge applied through the patient's body produces bad scars and is hard to control.

SUMMARY OF THE INVENTION

Accordingly, the present invention provides a surgical cutting instrument having a blade portion and cutting edge therefor which is adapted with electric input elements for cutting the tissue and cauterizing the surfaces of the incision, thereby allowing surgery to be more rapidly performed. This is accomplished in accordance with the illustrated embodiments of this invention by applying electrodes of opposed polarity to the blade near the cutting edge. With an electrical potential applied, no current will flow between the electrodes and no heat is produced unless the electrode gap is bridged by a conducting medium, such as moist tissue rendered conductive by the presence of physiological fluid. Heat is then generated by electric discharge below an arcing threshold in all areas where the blade is in contact with moist tissue. No electric discharge or heat occurs elsewhere. Moreover, if movement of the blade is halted, heat generation will automatically diminish as the tissue becomes dry as a result of cauterization. Cauterization and hemostasis may occur in both intact and incised tissue.

The electrodes may be made of films of platinum, palladium and other stable metals or alloys satisfying physiological requirements. While the potential applied may be DC or AC, the latter is preferred. In AC mode of operation, particularly at higher frequencies, the system will react as a lossy capacitor when a high conductivity material such as salt-containing water appears within the electrode gap or fringing field between electrode segments. In this case, the heating effect can be controlled by frequency modulation.

The substrate or blade is formed of an insulating material, preferably a glass or glass-ceramic or ceramic with fine grains. The present invention may take various forms for example:

(a) a substrate either conductive or non-conductive having interleaved alternate layers of conductors and insulators near the cutting edge to produce heating by conduction or discharge through the moist incised tissue;

(b) sets of longitudinal electrodes applied to one or both sides of blade having interleaved conductive fingers;

(c) a metallic cutting edge providing a common connection to one electrode on both sides of the blade; or (d) one electrode connected on each side of blade, interleafing across the cutting edge.

Herczog describes the embodiments (b) and (d) in U.S. Application Ser. No. 961,192 filed this same date and assigned to Corning Glass Works, the assignee herein.

The handle of the cutting instrument is electrically insulated from the blade. To permit comfortable use of the instrument, the handle and blade are lightweight detachable modules for easy replacement and interchangeability with blades having cutting edges of various shapes and sizes determined by the nature of the incision to be made and the tissue to be cut.

DESCRIPTION OF THE DRAWINGS

FIG. 1 is a schematic view illustrating, in end section, a preferred embodiment wherein the basic principle of operation of the present invention is described.

FIG. 2 is a pictorial view of another embodiment of the cutting instrument according to the present invention wherein a set of layered electrodes are applied to both sides of the blade.

DESCRIPTION OF THE PREFERRED EMBODIMENT

Figure 3:
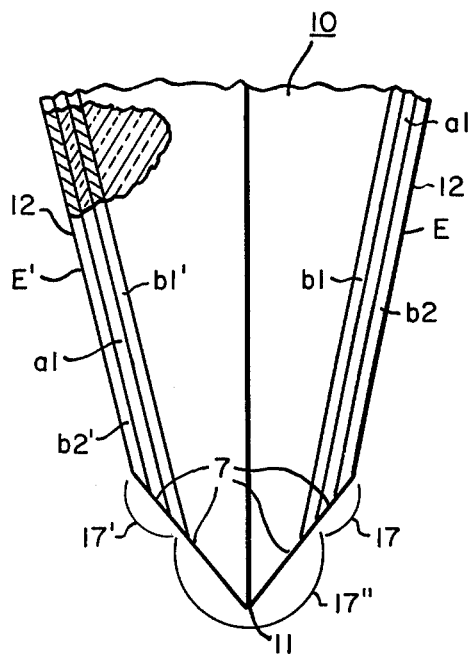
FIG. 3 is a partially fragmented end view of the blade illustrated in FIG. 2 along line 3—3 thereof.

In FIG. 1 there is shown in schematic from a preferred embodiment of the present invention illustrating the basic principle of operation. A substrate of an insulating material forms a surgical instrument or blade 10 having a cutting edge portion 11. The blade 10 carries electric input elements 12 which are conductive and are labeled respectively as electrodes E and E' for right and left sides of the blade 10. The input elements 12 may be metal foil overlays or coatings. Conductors 13 are electrically coupled to input elements 12 via leads or contacts 18 and are supplied with high frequency electrical energy. Tissue 14 is incised at 15 by the cutting edge 11 and incision 15 exposes surfaces 15a–15b being moistened by the presence of conductive physiological or body fluid 16. The electrical power is conducted to cutting edge 11 via the electric input elements 12 and, physiological fluid 16 provides one or more paths 17 for current conduction from one electrode E to the other E'. AC is preferred since, muscular stimulation, resulting from undesirable polarization of electrodes E-E', is possible when DC is used. Further, high frequency AC of 100 kHz–10 mHz is preferred since the input voltage can be as low as 30–50 volts, well below a threshold for arcing.

As the incision 15 is cauterized by the heat generated along conduction paths 17, the body fluid 16 is dried by the heating action. Thus conduction paths 17 are reduced substantially or essentially disappear and the process is self-limited. As the incision 15 is lengthened or deepened the newly incised tissue being moist due to the presence of body fluid 16 becomes conductive and allows the current to flow in that newly moistened area. The present invention does not require complex control of portions or segments of the blade 11 since the current paths 17 are produced only when the tissue 14 in incision 15 is moist, i.e. there is body fluid 16 present resulting from a fresh incision. Wide temperature excursions causing overheating of tissue or portions of the blade 10 is thereby eliminated.

The present invention will be further described below mainly with respect to incised tissue but it should be understood that incision is not absolutely necessary for the invention to provide hemostasis. The normally moist tissue of a human may be cauterized by the application of electrical energy in accordance with the principles of the present invention since the moist fluid associated with tissue conducts. Thus successful experiments using various forms of animal tissue have shown that the desired effect of cauterization can occur merely by placing the instrument 10 in contact with moist tissue. As physiological fluid dries the process diminishes to a low level but may continue if the instrument is left in one position. The principle described herein does not therefore require incision, release of fluid and cauterization to produce hemostasis as a multistep process but in reality requires the passage of electrical energy through any available electrolytic medium in or on the tissue surfaces to be cauterized. For purposes of explanation however, the main thrust of the disclosure will refer to the practice of incising and cauterizing tissue simultaneously.

Referring now to FIGS. 2 and 3 of the drawing, there is shown another preferred embodiment of the present invention, wherein similar elements illustrated and explained with regard to FIG. 1 are referenced with the same numerals. The surgical cutting instrument 10 includes the blade cutting edge 11 formed in the desired shape of a surgical cutting instrument which is detachable from handle or holder 9. The blade 10 may sometimes hereinafter be referred to as a substrate as it carries the electrical input elements 12 thereon disposed in the region of the cutting edge 11. Electrical connections 13 couple input elements 12 to a high frequency voltage source 8 via contacts 18 cable 19. The input elements 12 may be comprised of electrodes E and E' formed in layers of continuous conductive films or foils b1 and b2 being interleafed or layered with an insulating material or film a1+a2 each successively deposited on substrate 10. Layering of conductive films b1, b2, etc., and insulation a1+a2 may use conventional vapor-deposition processes, metal foil and film lamination techniques or other concepts hereinafter described.

In FIG. 3 a partially fragmented end view illustrates front portions of the right and left sides of blade 10. The elements on each side of the blade are similar and are labeled with the same reference numerals for corresponding portions except that the left side references are primed. The conductive films b1, b2-b1', b2' used for the input elements 12-12' may be tin oxide or other similar material. Electrical energy from high frequency voltage source 8 is delivered on both sides of blade 10 to respective conductive films b1 and b2, b1' and b2'. The high frequency signal cannot bridge the insulated spaces 7 between the conductive films b1 and b2 unless there is a conductive medium (e.g. body fluid 16) bridging the gap. Thus, if the cutting edge 11 of blade 10 were in a conductive fluid, current would flow between conductive films b1 and b2 and b1' and b2'. FIG. 3 illustrates conductive paths 17 and 17' and 17''. Conduction can occur between films on one side or across the cutting edge 11 depending on the relative polarity of films b1, b2 and b1', b2'.

As mentioned previously, it is contemplated, in the present invention that the tissue 14 is conductive due to the presence of body fluid 16 bound up in cells (not shown), on the surfaces of intact tissue or surfaces of newly incised tissue, (see FIG. 1). Such fluid satisfactorily conducts electricity. Once the region of the incision 15 is cauterized, the fluid 16 in the vicinity of the incision or area of contact with blade 10 dries and the electrical current reduces by a self-limiting process. This localizes the portion of the input element 12 in which power is dissipated to the portion in contact with moist tissue 14 (see FIG. 1). The tissue temperature near such portions of the input element 12 may thus be maintained at a sufficiently high temperature to effect cauterization and hemostasis.

Figure 4:
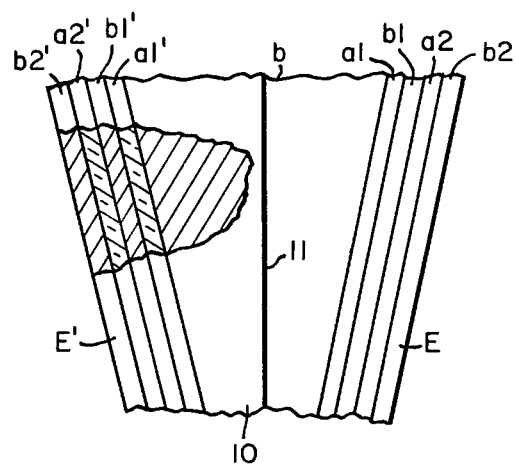
FIGS. 4 and 5 are fragmented end section views of variations on the embodiment of the present invention illustrated in FIG. 2, showing respectively a metallic cutting edge with interleaved layered electrodes and insulators, and a monolith blade structure.
Figure 5:
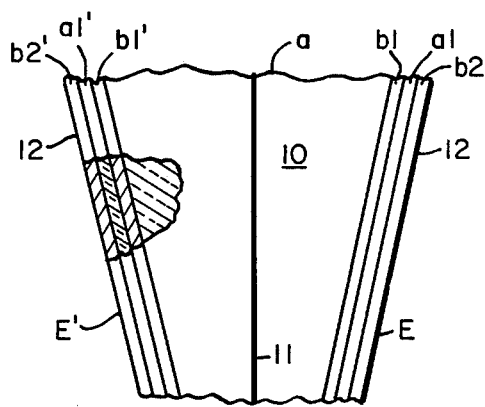

FIGS. 4 and 5 are variations of the present invention shown in partially fragmented end section. In FIG. 4 the blade or substrate 10 is formed of conductive material b. Insulating layers a1, a1' and a2, a2' are interleaved with conductive films b1, b1' and b2, b2' to form electrodes E and E'. The blade 10 may be used as a common terminal, electrically interacting with the conductive films b1,b1', b2,b2', etc.

In FIG. 5 the blade 10 may be a ceramic monolith of insulating material a having respective interleaved layers of co-fired or successively fired conductive and insulating films a1 ... b1 ... and primed counterparts on opposite sides of the cutting edge 11.

In FIGS. 2-5 the substrate 10 has a small and well controlled interelectrode spacing imposed very close to the cutting edge 11 by laminating the thin layers ($10\mu$ to $100\mu$) of the alternate layers of respective dielectric and conductive films or foils a1 ... and b1 ... In this arrangement wear of the blade cutting edges 11 will not drastically affect the spacing of the conductor configuration.

Typical materials usable as a dielectric are polymeric membranes, lacquer films, glazing, mica sheets, etc. Metals for electrodes can be chosen from precious and semiprecious metals mentioned above, as well as stainless steels and others, depending on the intended use. In the case of the monolithic structure of FIG. 5, it is possible to cofire screened-on dielectrics a1 ... and conductive films b1 ... as well as leads 13 and contacts 18 (not shown in FIG. 5). This approach allows a better control of the planarity of the cutting edge 11 and heating surfaces of the blade 10.

In FIG. 1 the spacing of the electrodes E-E' with respect to the cutting edge 11 should be accomplished by a narrow interelectrode spacing d, i.e. the distance d equals the path length from one electrode to the other across cutting edge 11. For input element 12, running parallel to the cutting edge 11, the spacing d is twice the distance d/2 from the cutting edge 11 to each of the electrodes E and E'.

In FIG. 1 electrodes E-E' may have a spacing d of 1.5 millimeters (d/2 0.75 millimeters) and be powered with high frequency (100 kilohertz) power of 100 volts or less, without arcing. The dimension d may preferably range from about 0.1 to 1.0 mm if desired. Low voltage is preferred generally from about 20 to 80 V.

An important advantage of the use of closely spaced electrodes E-E' is that the low voltage essentially eliminates arcing typical for most high frequency electrosurgical devices presently known. At low voltages, without arcing, flow of electricity between opposite electrodes is possible only by contact with moist tissue 14 containing high conductivity physiological fluids 16.

With cauterizing, the incised tissue 15 surfaces become dry and the conductive connection between electrodes E-E' ceases because the voltage is not sufficient for arc formation. This feature has the advantages of avoiding tissue burns, self-limiting control of electric power, and constant voltage control with respect to cutting rate or variation thereof in the area of the tissue to be incised at any instant in time.

For purposes of explanation, the arrangement of FIG. 1 will be detailed bearing in mind that the other embodiments of the present invention described herein have similar profiles. The substrate or blade 10 may be manufactured from a hard glass, glass-ceramic or ceramic sufficiently fine grained or homogeneous and strong for making a good cutting edge. The thickness of the blade 10 decreases to about 0.15 millimeters near the cutting edge 11. Two strips of metal foil, or metal coatings b-b' are applied to both sides of the blade 10 before the cutting edge 11 is formed. In this manner one assures that the electrodes E-E' are placed as close as possible to the cutting edge 11 which is formed by removal of some of the material of the heating element 12. For example Corning Code 1723 glass can be sealed to molybdenum foil by pressing in a vacuum at elevated temperature above the softening point of the glass. Other glasses and ceramics can be used with matched thermal expansion by sealing foils or by other metallizing processes. For very thin metal films (less than 1 millimeter) or films made from ductile metal such as aluminum, silver, platinum, gold, etc., matching thermal expansion is less critical.

For the blade 10 illustrated in FIG. 1 strips of 0.1 millimeter molybdenum metal cover the tapered portion 26 of the substrate 10 near the cutting edge 11. Such a coating of foil also provides for some reinforcement of the substrate 11 in the tapered portion 26. If thin electrically conductive films are used for the input element 12, the glass in the tapered region 26 could be formed thicker for providing more strength. Thin metal films of less than one millimeter are preferably made of tin oxide, platinum or gold or alloys thereof because of their good adherence to the substrate 10 and their electrochemical stability.

It has been mentioned that the operation is self-controlling if the voltage is kept at a certain value below the threshold for arcing. For the device shown in FIG. 1 the voltage may be in the range of about 50 to 20 volts as determined by the spacing between the electrodes E-E' near the cutting edge 11. Any decrease in the spacing of the electrodes E-E' will decrease the required voltage. Power dissipation will vary with the cutting rate and the contact area with the incised tissue at 15, and it is contemplated that the range of power dissipation is between about 5 and about 50 watts. High frequency power is used to minimize nerve stimulation and to avoid electrical polarization of the incision 15 including side reactions. The range of frequencies that has been found useful is between about 10 kilohertz and 10 megahertz. With such a wide frequency range a power supply having a variable frequency output can be used as a means of impedance matching the circuit of the power supply with the circuit of the surgical instrument 10 including the input element 12, and the electrical connections coupling power thereto. Generally the power supply setting should be chosen so as to maximize power at the lowest possible voltage for a given blade configuration.

The present invention is useful for other applications requiring a heated cutting edge, not withstanding the main thrust of the disclosure for a surgical instrument. For example the invention could be used to cut materials which are electrically conductive or rendered conductive by the presence of working fluids and the like, so that cutting and perhaps sealing could simultaneously occur.

While there have been described what are considered to be the preferred embodiments of the present invention it will be obvious to one skilled in the art that various changes and modifications may be made therein without departing from the invention and it is intended in the appended claims to cover all such changes and modifications which fall within the true spirit and scope of the invention.

We claim:

1. A surgical instrument adapted to be coupled to a source of electrical power for cauterizing tissue which is moist and electrically conductive due to the presence of physiological fluid and for simultaneous hemostasis thereof, the instrument comprising:

a blade, a cutting edge formed integrally with said blade along an edge thereof for incising tissue, and at least one pair of electrically-conductive electrodes adapted to be electrically coupled to the source of power, said electrodes disposed in the vicinity of said cutting edge having conductive surfaces to contact tissue which are disposed in spaced relationship on the blade adjacent to and oriented substantially parallel with each other and the cutting edge, wherein a plurality of parallel current paths are oriented substantially transversely with the cutting edge to conduct electrical power from one electrode to the other for directly heating the tissue in response to the electrical power applied to said electrically conductive electrodes and connection means on said surgical instrument providing electrical connections to said electrodes for supplying the electrical power thereto, the spacing of the electrodes being from about 0.1 to 1.0 mm one from another for carrying average electrical power of a magnitude of from about 5 to 50 watts without producing an electrical arc from one electrode to another.

2. The surgical instrument as in claim 1 wherein said electrodes are disposed on opposite sides of the blade and the parallel current paths traverse the cutting edge.

3. The surgical instrument as in claim 1 wherein said electrodes are disposed such that at least one lies along said cutting edge.

4. The surgical instrument of claim 1 wherein said electrodes are formed in alternate layers of dielectric and conductive materials.

5. The surgical instrument of claim 1 wherein said blade and electrodes are formed in a monolith of alternate layers of conductive and insulative material.

6. The surgical instrument of claim 1 wherein said electrodes comprise a plurality of conductive films each insulatively separated from one another and disposed in adjacent positions along each side of the cutting edge.

* * * * *